United States Patent [19]

Shimoyama et al.

[11] Patent Number: 4,993,430
[45] Date of Patent: Feb. 19, 1991

[54] ELECTRODE DEVICE FOR HIGH FREQUENCY THERMOTHERAPY APPARATUS

[75] Inventors: Jun Shimoyama, Kyoto; Akitoshi Miki, Toyonaka, both of Japan

[73] Assignee: Omron Tateisi Electronics Co., Kyoto, Japan

[21] Appl. No.: 398,496

[22] Filed: Aug. 25, 1989

Related U.S. Application Data

[63] Continuation of Ser. No. 141,398, Jan. 6, 1988, abandoned.

[30] Foreign Application Priority Data

Jan. 6, 1987 [JP] Japan .................................. 62-401

[51] Int. Cl.$^5$ .............................................. A61N 5/00
[52] U.S. Cl. .................................. 128/784; 128/401; 128/788; 128/804
[58] Field of Search ................. 128/784, 788, 804, 401

[56] References Cited

U.S. PATENT DOCUMENTS

| | | | |
|---|---|---|---|
| 2,074,634 | 3/1937 | Ackerman | 128/401 |
| 2,085,644 | 6/1937 | Ferciot | 128/788 |
| 2,346,245 | 4/1944 | Zichlin | 128/401 |
| 4,658,836 | 4/1987 | Turner | 128/804 |
| 4,662,383 | 5/1987 | Sogawa et al. | 128/401 X |
| 4,676,258 | 6/1987 | Inokuchi et al. | 128/804 |

FOREIGN PATENT DOCUMENTS 1145279  3/1963  Fed. Rep. of Germany .
2407559  8/1975  Fed. Rep. of Germany .

Primary Examiner—Lee S. Cohen
Attorney, Agent, or Firm—Fish & Richardson

[57] ABSTRACT

The disclosed electrode device for high frequency thermotherapy apparatus comprises a base member; a cavity-inserted cylindrical body removably fixed to the base member and inserted into a cavity of a living body; a separator fixed to the base member and arranged in the cylindrical body, for partitioning a space within the cylindrical body into two; an electrode arranged at an end of the separator; and in particular a circulation passage for a cooling liquid being formed extending from a going path, through an end space, to a return path within the cylindrical body. Therefore, the surface of the living body in contact with the cylindrical body can be efficiently cooled by circulating a cooling liquid therethrough to protect the surface of the living body from being heated excessively. Further, the cavity-inserted cylindrical body can be replaced or removed for washing to realize a sanitary medical treatment.

2 Claims, 2 Drawing Sheets

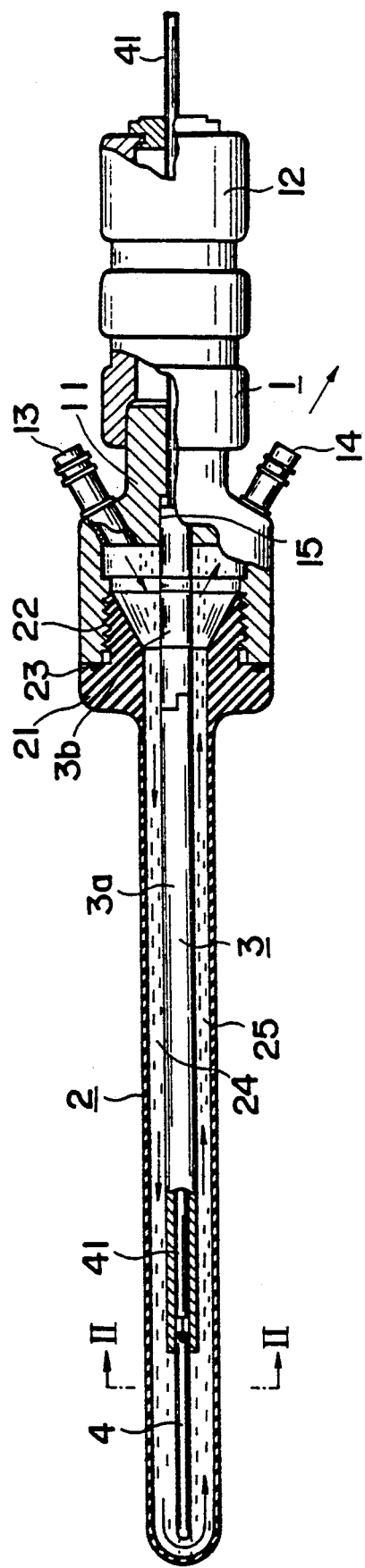
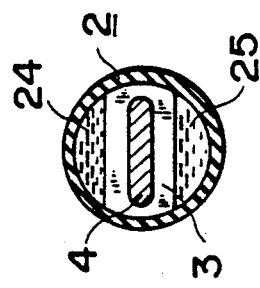

ELECTRODE DEVICE FOR HIGH FREQUENCY THERMOTHERAPY APPARATUS

This application is a continuation of U.S. application Ser. No. 191,398, filed Jan. 6, 1988, now abandoned.

BACKGROUND OF THE INVENTION

1. Field of the Invention

The present invention relates to an electrodes device for high frequency themotherapy apparatus, which is inserted into a cavity of a living body (an organism), for instance, such as rectum to effect medical treatment against cancer cells at moderately warm temperature.

2. Description of the Prior Art

An electrode device used for high frequency thermotherapy apparatus is generally called applicator. This applicator is made up of an electrode section for applying a high frequency electric field and a cooling section for cooling the skin for protection from burn. A high frequency thermotherapy apparatus is provided with a pair of applicators. In the thermotherapy, one applicator is inserted into a cavity of a living body (e.g. into the rectum from the anus), while the other applicator is arranged on the outer surface of the living body so as to sandwich the disease part between the two applicators. A high frequency electric field is generated between the two applicators to warm or heat the disease part (e.g. cancer cells) for thermotherapy. To cool or protect the inner and outer surface of a living body in contact with these applicators from heat, a cooling device is required for the applicator.

For the applicator arranged outside the body, since the shape of the applicator can be increased easily, it is possible to provide a sufficiently wide cooling space and surface. For the applicator to be inserted into a very narrow cavity of a living body (patient), however, it is impossible to increase the diameter of the applicator (a cavity-inserted cylindrical body). Therefore, the space within the inserted cylindrical body is extremely narrow. In other words, the space where an electrode is arranged or a cooling liquid is passed is every small in volume. In addition, in the prior-art cavity-inserted cylindrical body, since a cooling liquid charging port and a cooling liquid discharge port are only arranged, there exists a problem in that cooling liquid will not flow or circulate and therefore the cooling efficiency is low. When the cavity is not sufficiently cooled, there exists a danger that the mucous membrane is burnt.

SUMMARY OF THE INVENTION

The object of the present invention is to provide an electrode device for high frequency thermotherapy apparatus, which can be cooled sufficiently and inserted into a small cavity of a living body.

To achieve the above-mentioned object, an electrode device for high frequency thermotherapy apparatus of the present invention having (a) a base member; (b) a cavity-inserted cylindrical body fixed to the base member; (c) a separator fixed to the base member and arranged in the cavity-inserted cylindrical body along the longitudinal direction thereof, for partitioning a space within the cavity-inserted cylindrical body into two except an end space thereof; (d) an electrode arranged at an end of the separator; and (e) a circulation passage for a cooling liquid being formed extending from a first space partitioned by the separator within the cavity-inserted cylindrical body, through the end space of the cylindrical body, to a second space partitioned by the separator.

In the electrode device of the high frequency thermotherapy apparatus as described above, the inner space within the cavity-inserted cylindrical body is perfectly divided into two by the separator to form a circulation passage for a cooling liquid. Therefore, the cooling liquid supplied from a liquid charge port provided at the base member smoothly flows into the cavity-inserted cylindrical body, turns around the end of the electrode portion, and returns to a discharge port also provided at the base member. Therefore, the cooling liquid is not pooled within the cylindrical body and not heated to a high temperature as in the prior-art device, but the cooling liquid is always circulated to cool the device efficiently. Since the warming target (disease part) can be efficiently warmed without heating the surface of the cavity into which the cylindrical body is inserted, the effect of the thermotherapy apparatus can be improved.

In particular, it is preferable that the electrode device is constructed in such a way that the cavity-inserted cylindrical body is removably connected to the base member under liquid tight condition. This is because the cavity-inserted cylindrical body can be removed for washing and replaced with a washed one or new one, thus enabling a sanitary medical treatment.

BRIEF DESCRIPTION OF THE DRAWINGS

FIG. 1 is a front view, partly broken, showing an embodiment of electrode device for high frequency thermotherapy apparatus of the present invention;

FIG. 2 is an enlarged cross-sectional view taken along the line II—II shown in FIG. 1;

DETAILED DESCRIPTION OF THE PREFERRED EMBODIMENTS

Figure 3:
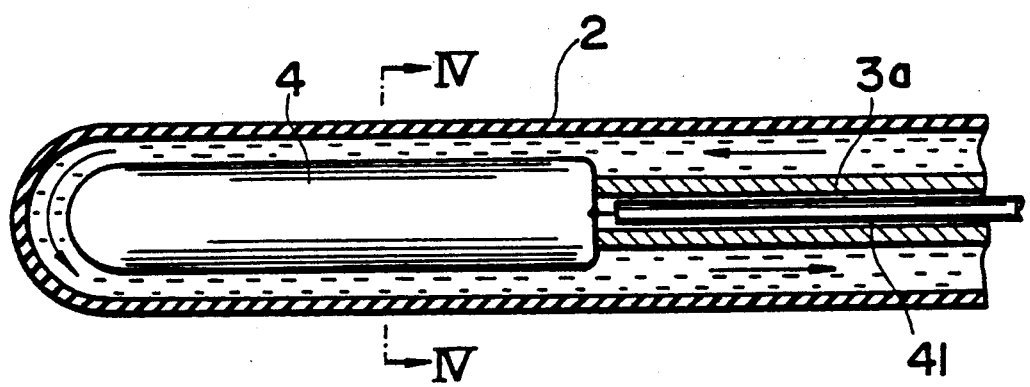
FIG. 3 is an enlarged cross-sectional view showing an essential portion of another embodiment of the electrode device for high frequency thermotherapy apparatus of the present invention.

FIG. 1 is a front view, partly broken, showing an embodiment of the electrode device for high frequency thermotherapy apparatus of the present invention, and FIG. 2 is an enlarged cross-sectional view taken along the line II—II shown in FIG. 1.

As described above, the high frequency thermotherapy apparatus includes a pair of applicators each provided with an electrode section for applying a high frequency electric field to a diseased part and a cooling section for cooling and protecting the skin surface of the body corresponding in position to the diseased part (warming or heating target). One of the applicator is inserted into the cavity of the living body, and the other of the applicator is arranged on the outer skin surface of the body at such a position as to correspond to the warming target so as to be opposed to each other.

The applicator attached to the outer skin surface of the body is the same in structure as the conventional one, therefore the description thereof being omitted herein. The applicator inserted into a cavity will now be described hereinbelow.

In FIG. 1, an applicator inserted into a cavity (an electrode device for high frequency thermotherapy apparatus) comprises a base number 1, a cylindrical body 2 to be inserted into a cavity, a separator 3, and an electrode 4.

The base member 1 includes a cylindrical member 11 having an open end and a bottom and a connector 12 fixed to the bottom of the cylindrical member 11. A female thread is formed on the inner circumferential surface of the open end of the cylindrical member 11 so as to be coupled to the cavity-inserted cylindrical body 2. A pipe-shaped liquid charge port 13 and a pipe-shaped liquid discharge port 14 are provided on both sides of the bottom of the cylindrical member 11. To these two ports 13 and 14, a cooling device of forced circulation type (a cooling liquid is forcedly circulated) is connected. A fitting hole 15 to which a base portion of the separator 3 is fitted is formed at the center of the bottom surface of the cylindrical member 11.

The separator 3 is composed of a liquid passage partition plate 3a of a flat type having a width roughly equal to an inner diameter of the cavity-inserted cylindrical body 2 and a liquid charge/discharge partition plate 3b of a flat type having a width changing according to the inner diameter of the cylindrical body 2 and to the inner diameter of the cylindrical member 11 and roughly equal to these diameters. The partition plate 3b is fixedly fitted to a fitting hole 15 formed in the cylindrical member 11. The partition plate 3a is removably connected to the partition plate 3b near the base portion of the cylindrical body 2.

A flat electrode 4 of elongated oral shape in cross section is fixedly fitted to an end portion of the liquid passage partition plate 3a. A lead wire 41 of the electrode 4 is passed through a hole formed in the liquid passage partition plate 3a, the liquid charge/discharge partition plate 3b, and the base 1 (i.e. cylindrical member 11 and the connector 12), toward the outside.

The cavity-inserted cylindrical body 2 is made of an electrically insulating material and is rounded at an end thereof. The base portion of the cylindrical body 2 is formed into a large diameter portion 21. A male thread is formed at this large diameter portion 21. When this male thread is screwed into the female thread of the cylindrical member 11 (the screwed portion is designated by reference numeral 22), the cylindrical body 2 is removably fixed to the base 1 under liquid tight condition via an O ring intervening between two end surfaces of the cylindrical body 2 and the cylindrical member 11.

Where the cavity-inserted cylindrical body 2 is connected to the base 1, the liquid passage partition plate 3a (including the electrode 4) which constitutes the separator 3 is positioned within the cylindrical body 2 in such a way that a slight space is formed between the end of the electrode 4 and the inner end portion of the cylindrical body 2 and further the inner space within the cylindrical body 2 is bisected (divided into two upper and lower spaces) by the liquid passage partition plate 3a so as to provide a liquid going patn 24 on the upper side and a liquid return path 25 on the lower side. Since the inner space of the cylindrical member 11 is also bisected into the upper portion and the lower portion by the liquid charge/discharge partition plate 3b, the liquid charge port 13 communicates with the liquid going path 24 and the liquid discharge port 14 communicates with the liquid return path 25, thus establishing a cooling liquid circulation passage.

Figure 4:
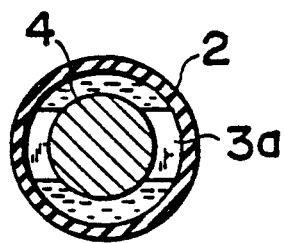
FIG. 4 is an cross-sectional view taken along the line IV—IV shown in FIG. 3.

FIG. 3 is a cross-sectional view of a modification of the electrode 4, and FIG. 4 is a cross-sectional view taken along the line IV—IV in FIG. 3.

In the embodiment shown in FIGS. 1 and 2, a flat plate-shaped electrode 4 is used. In this modification, a cylindrical electrode is adopted, as shown in FIG. 4, to more efficiently warm the target part.

When the electrode device for high frequency thermotherapy apparatus as described above is used to remedy rectum cancer, for instance, the cavity-inserted cylindrical body 2 is inserted into the anus of a patient and the electrode 4 is positioned at the position corresponding to a warming target (disease part). In this case, when scales or graduations are marked on the outer surface of the cavity-inserted cylindrical body 2, since the insertion depth can be known easily, it is possible to accurately position the electrode 4 at the position corresponding to the warming target. When a cooling liquid is supplied from the liquid charge port 13 into the cylindrical member 11 (the base 1), the cooling liquid flows through the going path 24, turns around the electrode 4, and returns through the return path 25, being discharged toward the outside from the discharge port 14. Since the whole of the electrode 4 and the cavity-inserted cylindrical body 2 is always cooled by the circulating cooling liquid, the outer surface of the living body in contact with the cylindrical body 2 can be cooled for protection against burn, in particular the surface near the electrode 4 is sufficiently cooled, so that only the diseased part between the two applicators can be efficiently warmed.

Further, since the cavity-inserted cylindrical body 2 is removably attached to the base member 1, it is possible to remove the cylindrical body 2 from the base member 1 for washing or to replace the body 2 with a new one, thus securing a sanitary medical treatment.

As described above, since the base member and the cavity-inserted cylindrical body are removably connected and further a liquid circulating path is formed within the cavity-inserted cylindrical body by the separator attached to the base member, it is possible to smoothly circulate the cooling liquid via the going and return paths even if the internal space of the cavity-inserted cylindrical body is extremely small. Therefore, since the surface of the living body in contact with the electrode device is always cooled without being heated into a burn, it is possible to effectively warm or heat warming target (disease part) at appropriate temperature irrespective of the position of the warming target.

Further, since the cavity-inserted cylindrical body can be removed from the base member, it is possible to replace the cavity-inserted cylindrical body with a new one or wash the cylindrical body for each medical treatment, thus realizing a sanitary medical treatment.

What is claimed is:

1. An electrode device for high frequency thermotherapy apparatus, comprising;
    (a) a base member having a cooling liquid charge port and a cooling liquid discharge port;
    (b) a cavity-inserted cylindrical body removably fixed to said base member under liquid-tight conditions;
    (c) a separator fixed to said base member and arranged in said cavity-inserted cylindrical body along the longitudinal direction thereof, partitioning a space within said cavity-inserted cylindrical body into a first and a second space except for an end space thereof, said first space communicating with said charge port and said second space communicating with said discharge port, said separator comprising a flat liquid passage partition plate having a width substantially equal to an inner diameter of said cavity-inserted cylindrical body coupled to a flat liquid charge/discharge partition plate fixed to said base member having a width substantially equal to an inner diameter of said base member;

(d) an electrode arranged at one of said separator extending into said end space; and (e) a circulation passage for a cooling liquid being formed extending from said first space via said end space to said second space.

2. An electrode device for high frequency thermotherapy apparatus according to claim 1, wherein the liquid passage partition plate and the liquid charge/discharge partition plate are separate pieces which are coupled together.

* * * * *